(12) United States Patent
Shahriari

(10) Patent No.: US 12,167,958 B2
(45) Date of Patent: *Dec. 17, 2024

(54) MULTI-SPIRAL SELF-EXPANDING STENT AND METHODS OF MAKING AND USING THE SAME

(71) Applicant: Ascyrus Medical, LLC, Boca Raton, FL (US)

(72) Inventor: Ali Shahriari, Boca Raton, FL (US)

(73) Assignee: Ascyrus Medical, LLC, Boca Raton, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/867,666

(22) Filed: Jul. 18, 2022

(65) Prior Publication Data

US 2022/0346937 A1 Nov. 3, 2022

Related U.S. Application Data

(63) Continuation of application No. 16/580,243, filed on Sep. 24, 2019, now Pat. No. 11,389,289, which is a
(Continued)

(51) Int. Cl.
*A61F 2/07* (2013.01)
*A61F 2/90* (2013.01)
*A61F 2/966* (2013.01)

(52) U.S. Cl.
CPC ............... *A61F 2/07* (2013.01); *A61F 2/90* (2013.01); *A61F 2/966* (2013.01);
(Continued)

(58) Field of Classification Search
CPC ...... A61F 2/07; A61F 2/82; A61F 2/90; A61F 2/88; A61F 2002/075; A61F 2230/0067;
(Continued)

(56) References Cited

U.S. PATENT DOCUMENTS 5,755,769 A 5/1998 Richard et al.
6,331,188 B1 12/2001 Lau et al.
(Continued)

FOREIGN PATENT DOCUMENTS

CN 103356315 A 10/2013
EP 2294989 A2 3/2011
(Continued)

OTHER PUBLICATIONS

Supplementary European Search Report for U.S. Appl. No. 18/771,411 dated Nov. 17, 2020.
(Continued)

*Primary Examiner* — Paul B Prebilic
(74) *Attorney, Agent, or Firm* — Meunier Carlin & Curfman LLC

(57) ABSTRACT

A multi-spiral, self-expanding stent is constructed from superposed individual spiral strands. Each spiral strand comprises a terminal bend that separates the strand into a first portion and a second portion. Particularly, the first portion of each strand bends in a first spiral direction to the terminal bend, and the second portion bends in the opposite direction after the terminal bend. Advantageously, the disclosed stent is able to change its shape, diameter, and length to accommodate the corresponding shape, diameter, and length of patient's diseased vessel.

20 Claims, 9 Drawing Sheets

Related U.S. Application Data continuation of application No. PCT/US2018/019569, filed on Feb. 23, 2018.

(60) Provisional application No. 62/475,934, filed on Mar. 24, 2017.

(52) U.S. Cl.
CPC . *A61F 2002/075* (2013.01); *A61F 2250/0007* (2013.01); *A61F 2250/001* (2013.01)

(58) Field of Classification Search
CPC ........ A61F 2230/0069; A61F 2240/001; A61F 2250/0007; A61F 2250/001; A61F 2250/0039
See application file for complete search history.

(56) References Cited

U.S. PATENT DOCUMENTS

| | | |
|---|---|---|
| 6,409,750 B1 | 6/2002 | Hyodoh et al. |
| 6,656,219 B1 | 12/2003 | Wiktor |
| 6,695,833 B1 | 2/2004 | Frantzen |
| 6,723,116 B2 | 4/2004 | Taheri |
| 6,918,925 B2 | 7/2005 | Tehrani |
| 7,273,493 B2 | 9/2007 | Ledergerber |
| 7,488,344 B2 | 2/2009 | Hartley et al. |
| 8,603,156 B2 | 12/2013 | Hartley et al. |
| 8,945,203 B2 | 2/2015 | Shalev et al. |
| 11,284,999 B2 * | 3/2022 | Tabor .................... A61F 2/2418 |
| 11,389,289 B2 * | 7/2022 | Shahriari .................. A61F 2/07 |
| 2003/0040771 A1 | 2/2003 | Hyodoh et al. |
| 2004/0039435 A1 | 2/2004 | Hancock et al. |
| 2004/0093068 A1 * | 5/2004 | Bergen .................... A61L 31/16 |
| | | 623/1.15 |
| 2004/0116945 A1 | 6/2004 | Sharkawy et al. |
| 2004/0116999 A1 | 6/2004 | Ledergerber |
| 2004/0167605 A1 | 8/2004 | Elliott |
| 2005/0090834 A1 | 4/2005 | Chiang et al. |
| 2006/0089704 A1 | 4/2006 | Douglas |
| 2006/0247760 A1 | 11/2006 | Ganesan et al. |
| 2009/0099650 A1 | 4/2009 | Bolduc et al. |
| 2009/0157158 A1 | 6/2009 | Ondracek et al. |
| 2009/0319017 A1 | 12/2009 | Berez et al. |
| 2010/0114291 A1 | 5/2010 | Kolbel et al. |
| 2010/0324649 A1 | 12/2010 | Mattsson et al. |
| 2010/0324650 A1 | 12/2010 | Keeble et al. |
| 2011/0265908 A1 | 11/2011 | Clerc et al. |
| 2012/0191174 A1 | 7/2012 | Vinluan et al. |
| 2012/0323300 A1 | 12/2012 | Greenberg et al. |
| 2013/0144373 A1 | 6/2013 | Shahriari |
| 2013/0166015 A1 | 6/2013 | Roeder |
| 2013/0289713 A1 | 10/2013 | Pearson et al. |
| 2014/0046428 A1 | 2/2014 | Cragg et al. |
| 2014/0277348 A1 | 9/2014 | Roeder |
| 2017/0128242 A1 | 5/2017 | Ding |

FOREIGN PATENT DOCUMENTS

| | | |
|---|---|---|
| JP | 2005270432 A | 10/2005 |
| JP | 2011502628 A | 1/2011 |
| KR | 20000042899 A | 7/2000 |
| WO | 00/44309 A2 | 8/2000 |
| WO | 2010105195 A2 | 9/2010 |

OTHER PUBLICATIONS

International Search Report for International Patent Application No. PCT/US2018/019659, dated Jun. 27, 2018, 5 pages.
Written Opinion for International Patent Application No. PCT/US2018/019659, dated Jun. 27, 2018, 8 pages.
International Preliminary Report on Patentability for International Patent Application No. PCT/US2018/019659, dated Sep. 24, 2019, 9 pages.
Office Action for Japanese Patent Application No. 2017-536857 dated Nov. 26, 2019.
Office Action for Japanese Patent Application No. 2018-206631 dated Oct. 23, 2019, 9 pages.
Communication Pursuant to Article 94(3) EPC issued for European Application No. 18771411.8, dated Aug. 28, 2024.

* cited by examiner

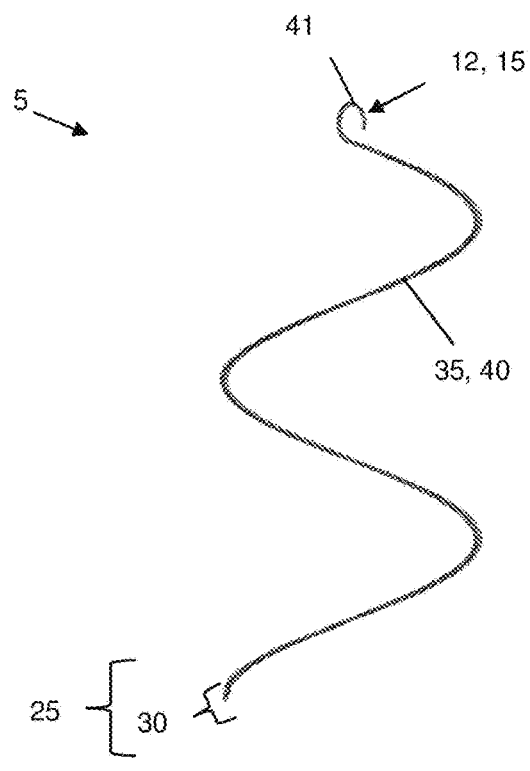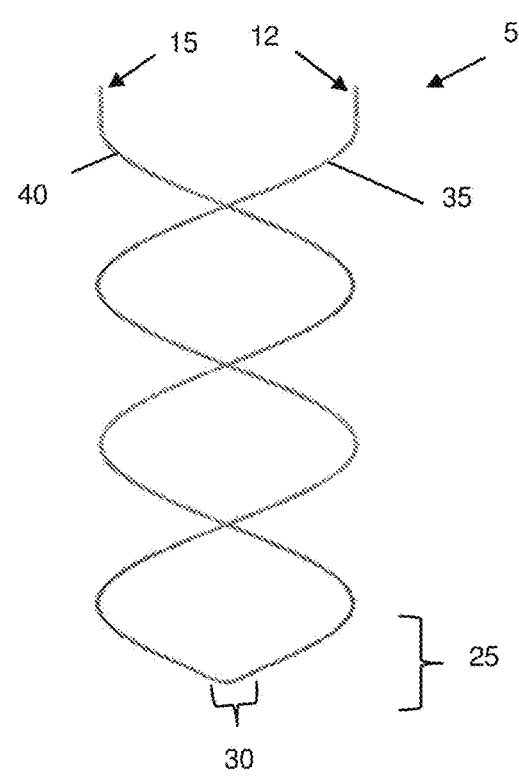
Fig. 2a                     Fig. 2b

MULTI-SPIRAL SELF-EXPANDING STENT AND METHODS OF MAKING AND USING THE SAME

CROSS REFERENCE TO RELATED APPLICATIONS

This application is a continuation of U.S. patent application Ser. No. 16/580,243, filed on Sep. 24, 2019, now U.S. Pat. No. 11,389,289 which is a continuation of PCT Patent Application No. PCT/US2018/019659, filed Feb. 26, 2018, which claims priority to and the benefit of U.S. Provisional Patent Application No. 62/475,934, filed Mar. 24, 2017, which are all incorporated by reference herein in their entireties.

TECHNICAL FIELD

The presently disclosed subject matter relates to a multi-spiral self-expanding stent, and to methods of making and using the disclosed stent.

BACKGROUND

Expandable stents are well known for the treatment of vascular maladies and aortic disease. Such stents are typically implanted within a blood vessel in a contracted state and expanded when inserted to maintain patency of the vessel and to allow fluid to flow therethrough. However, prior art stents are designed to fit vessels of relatively uniform diameter and length proximal and distal to the lesion. As a result, prior art stents are unable to conform the diameter and length to the changing diameters and curvatures of a patient's aorta. In addition, for the treatment of aortic dissection, prior art stents lack the required radial resistive force required for treatment of certain diseases (such as aortic dissections) and therefore demonstrate varying degrees of collapse in clinical use. Accordingly, it would be beneficial to provide a multi-spiral, self-expanding stent that overcomes the shortcomings of the prior art.

SUMMARY

In some embodiments, the presently disclosed subject matter is directed to a self-expanding stent. The stent comprises a plurality of strands, each strand including a first portion leading to a terminal bend forming a first end of the self-expanding stent and a second portion concluding in a plane at a second end of the self-expanding stent. The strand first and second portions are woven together to form the self-expanding stent. The first and second strand portions forming each of the strands are formed of a continuous material. The first strand portion of each strand bends in one spiral direction up the terminal bend, and the second strand portion bends in an opposite spiral direction after the terminal bend.

In some embodiments, the self-expanding stent further includes a graft collar at about the plane at the second end of the self-expanding stent. In some embodiments, the graft collar is reinforced by support from the strands. In some embodiments, the graft collar is reinforced by support from separate meandering wire strands.

In some embodiments, the strands are formed of metal, polymeric materials, or combinations thereof. In some embodiments, the metal is selected from stainless steel, gold, cobalt, chromium, molybdenum, nickel, titanium, nitinol, polypropylene, polycarbonate, nylon, high density polyethylene, or alloys or combinations thereof.

In some embodiments, the strands are bent or formed into shape on a mandrel while assembled into the self-expanding stent.

In some embodiments, the strands are bent or formed into shape before being assembled into the self-expanding stent.

In some embodiments, the self-expanding stent is configured to change its length and diameter to adjust itself to the diameter of a hollow tube; exert a minimal radial resistive force of at least 1N despite changing its length and diameter; and exert a maximum outward chronic force of 7N despite changing its length and diameter.

In some embodiments, the presently disclosed subject matter is directed to a kit comprising a self-expanding stent as disclosed herein and a deployment device.

In some embodiments, the presently disclosed subject matter is directed to a method of forming a self-expanding stent. Particularly, the method comprises spirally wrapping a first strand comprising a first end and a second end around a mandrel to produce a spiral strand with a first portion leading to a terminal bend forming a first end and a second portion concluding in a plane at a second end of the spiral strand. The first portion of each strand bends in one spiral direction up the terminal bend, and the second portion bends in an opposite spiral direction after the terminal bend. The method further comprises repeating for a desired number of strands to produce a desired number of spiral strands, and weaving the spiral strands together to create a hollow stent structure over the mandrel. The method further comprises removing the hollow stent structure from the mandrel, whereby a self-expanding stent is formed.

In some embodiments, each strand is formed of a continuous material.

In some embodiments, the method further comprises attaching the self-expanding stent to a graft collar at about the plane at the second end of the self-expanding stent. In some embodiments, the graft collar is reinforced by strand support.

In some embodiments, the presently disclosed subject matter is directed to a method of endovascularly repairing an aorta in a patient in need thereof. Particularly, the method comprises inserting a self-expanding stent as disclosed herein into the aorta, expanding the self-expanding stent, and translating the first end, second end, or both of the self-expanding stent to change the shape, diameter, length, or combinations thereof to accommodate the corresponding shape, diameter, length, or combinations thereof of the patient's aorta, whereby the aorta is repaired.

In some embodiments, the repairing comprises a repair of aortic valve disease, aortic stenosis, ascending aortic aneurysms, aortic insufficiency, aortic regurgitation, ascending aneurysm, bicuspid valve disease, aortic dissections, or combinations thereof.

In some embodiments, the method further comprises attaching the self-expanding stent to a graft collar at about the plane at the second end of the self-expanding stent.

In some embodiments, the presently disclosed subject matter is directed to a self-expanding stent comprising a plurality of strands, each strand including a first portion leading to a terminal bend forming a first end of the self-expanding stent and a second portion concluding in a plane at a second end of the self-expanding stent.

BRIEF DESCRIPTION OF THE DRAWINGS

FIG. 2a is a front perspective view of one embodiment of a spiral strand.

FIG. 2b is a side perspective view of the spiral strand of FIG. 2a.

FIG. 6b is a CT scan of the stent of FIG. 5, illustrating change from the resting position to an expanded position when deployed inside the aorta of FIG. 6a.

DETAILED DESCRIPTION

The presently disclosed subject matter is introduced with sufficient details to provide an understanding of one or more particular embodiments of broader inventive subject matters. The descriptions expound upon and exemplify features of those embodiments without limiting the inventive subject matters to the explicitly described embodiments and features. Considerations in view of these descriptions will likely give rise to additional and similar embodiments and features without departing from the scope of the presently disclosed subject matter.

Unless defined otherwise, all technical and scientific terms used herein have the same meaning as commonly understood to one of ordinary skill in the art to which the presently disclosed subject matter pertains. Although any methods, devices, and materials similar or equivalent to those described herein can be used in the practice or testing of the presently disclosed subject matter, representative methods, devices, and materials are now described.

Following long-standing patent law convention, the terms "a", "an", and "the" refer to "one or more" when used in the subject specification, including the claims. Thus, for example, reference to "a stent" can include a plurality of such stents, and so forth.

Unless otherwise indicated, all numbers expressing quantities of components, conditions, and so forth used in the specification and claims are to be understood as being modified in all instances by the term "about". Accordingly, unless indicated to the contrary, the numerical parameters set forth in the instant specification and attached claims are approximations that can vary depending upon the desired properties sought to be obtained by the presently disclosed subject matter.

As used herein, the term "about", when referring to a value or to an amount of mass, weight, time, volume, concentration, and/or percentage can encompass variations of, in some embodiments +/−20%, in some embodiments +/−10%, in some embodiments +1-5%, in some embodiments +/−1%, in some embodiments +1-0.5%, and in some embodiments +/−0.1%, from the specified amount, as such variations are appropriate in the disclosed packages and methods.

The presently disclosed subject matter relates to a multi-spiral, self-expanding stent. The term "stent" as used herein refers to any device or structure that adds rigidity, expansion force, and/or support when implanted in a body passageway (e.g., a lumen or artery). A stent is used to obtain and maintain the patency of the body passageway while maintaining the integrity of the passageway. The term "self-expanding" as used herein refers to the tendency of a stent to return to a predetermined, expanded diameter when unrestrained.

Figure 1:
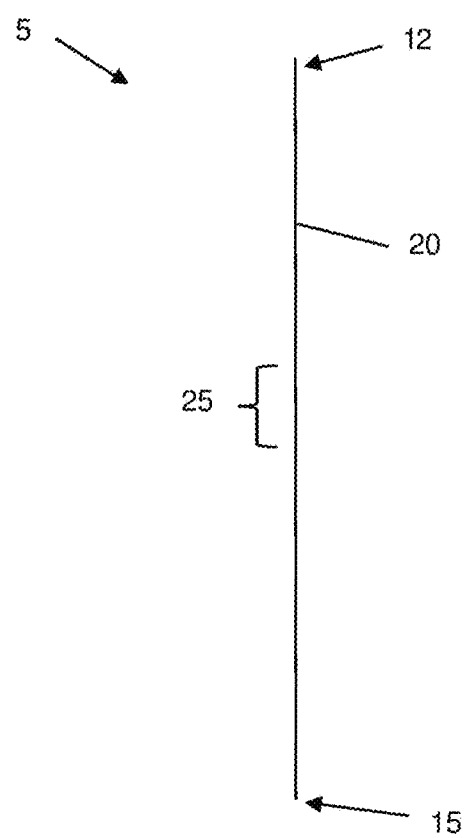
FIG. 1 is a front perspective view of a strand in accordance with some embodiments of the presently disclosed subject matter.
Figure 2C:
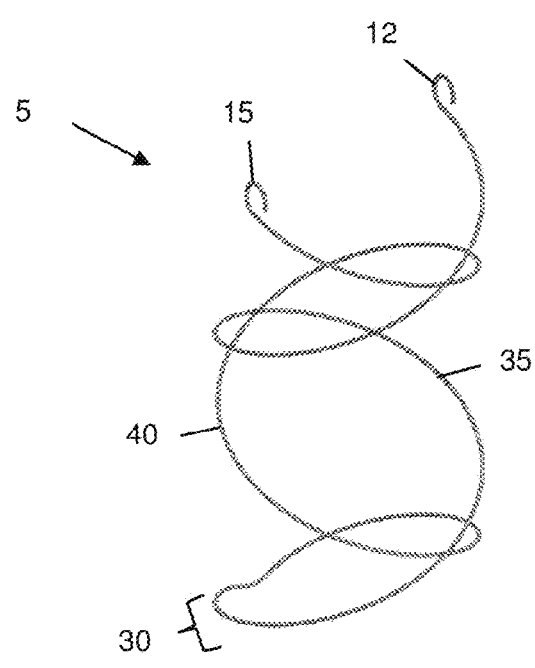
FIGS. 2c and 2d are isometric views of spiral strands in accordance with some embodiments of the presently disclosed subject matter.
Figure 2D:
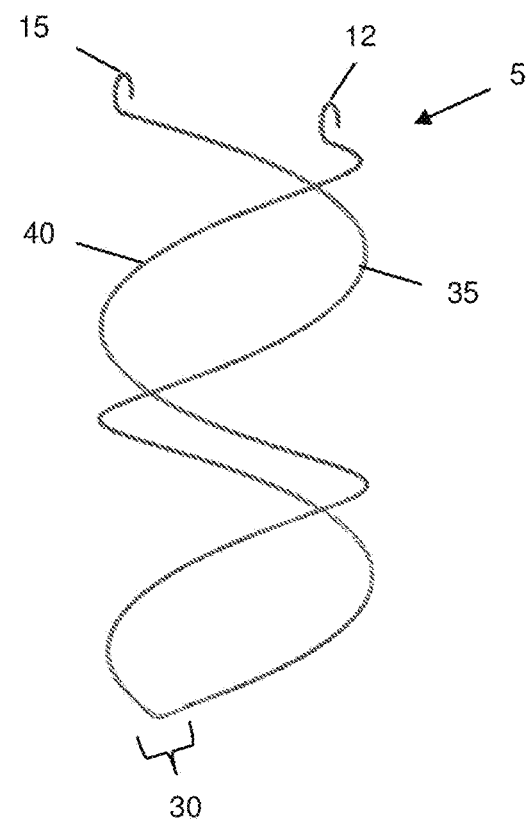

The disclosed multi-spiral stent is constructed from superposed individual spiral strands. Particularly, FIG. 1 illustrates one embodiment of strand 5 prior to bending in a spiral configuration. As shown, strand 5 comprises first end 12, second end 15, and continuous elongated body 20 that includes an approximate middle portion 25. In the disclosed spiral configuration, strand 5 includes terminal bend 30 that can be positioned at the approximate middle portion 25, as illustrated in the front and perspective views of FIGS. 2a and 2b and the isometric views of FIGS. 2c and 2d. Thus, as shown, spiral strand 5 comprises terminal bend 30 that separates the strand into first portion 35 and second portion 40. Particularly, first portion 35 of each strand bends in a first spiral direction to the terminal bend, and second portion 40 bends in the opposite direction after the terminal bend. The term "spiral" as used herein refers to a shape that generally resembles a helix as viewed in a 2-dimensional plane from a direction that is substantially orthogonal to the helix's axis of rotation, as exemplified in the figures. In some embodiments, the peaks and troughs of the first portion alternate with the peaks and troughs of the second portion in the spiral configuration. In some embodiments, the spiral comprises a single spiraling loop or more than one loop. In some embodiments, the single spiraling loop makes a turn of about 360 degrees.

Strand 5 can be constructed from any of a wide variety of biocompatible materials, including one or more metal and/or polymeric materials. Thus, suitable materials can include (but not limited to) stainless steel, gold, Elgiloy®, nickel, titanium, nitinol, polypropylene, polycarbonate, nylon, high density polyethylene, or combinations thereof. The term "biocompatible" as used herein refers to a material that is substantially non-toxic in the in vivo environment of its intended use, and that is not substantially rejected by the patient's physiological system (i.e., is non-antigenic). In some embodiments, the material used to construct strand 5 can be coated in a polymeric material, as would be known in the art. In an alternate embodiment, strands 5 can be constructed from a biodegradable material that is configured to degrade after healing of the aorta is accomplished.

The spiral can be constructed by helically winding strand 5 about a central or longitudinal axis. For example, in some embodiments, a strand can be spirally wrapped around a mandrel and then removed from the mandrel to produce a spiral of desired dimensions. The terminal bend can be formed by wrapping around another mandrel, pinched, or otherwise formed. In some embodiments, the transverse edges of the stent can be secured to retain the spiral configuration.

Figure 3:
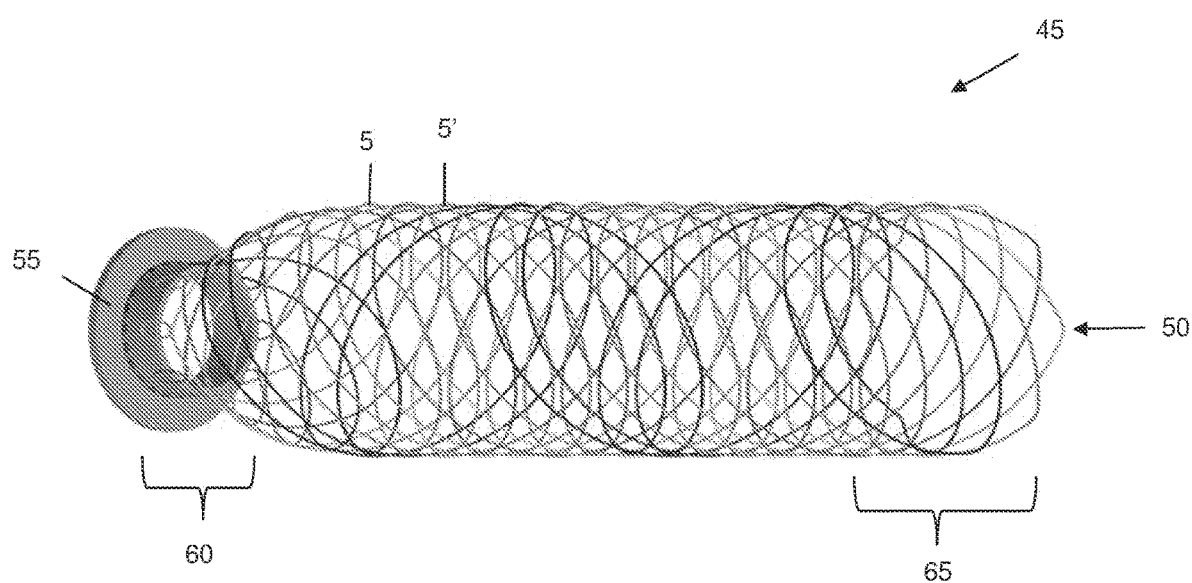
FIG. 3 is a perspective view of a straight configuration multi-spiral stent in accordance with some embodiments of the presently disclosed subject matter.

As illustrated in FIG. 3, each spiral strand 5 functions together with at least 3 other spiral strands (5') superimposed and woven together to create tubular stent 45 that includes passageway 50 therethrough. Thus, each strand includes a first strand portion leading to terminal bend 30 forming first end 60 of the self-expanding stent. The second portion of each strand bends in the opposite spiral direction after the terminal bend and concludes in a plane at second end 65 of the stent. The shape of the spiral strands in concert allow for creation of a stent that retains its physical properties. For example, the spiral shape of each portion of the strands are configured so as to not constrain movement during bending or compression and to minimize the likelihood of stress buildup that can cause kinking and radial resistive force. Thus, the configurations illustrated are exceptionally kink-resistive and flexible when flexed along the longitudinal axis of the stent.

Advantageously, the disclosed stent is also able to change its shape, diameter, and length to accommodate the corresponding shape, diameter, and length of a patient's diseased vessel, and particularly when the shape and diameter are not consistent along a length of the diseased vessel. Particularly, the stent diameter can be modified by translation of first and/or second ends 60, 65 to alter the stent length and thereby change the stent diameter. In other words, the stent diameter can be modified based on the forces it is exposed to that will lengthen or shorten it. Thus, the disclosed stent can have a diameter of about 50-60 mm and a length of about 90-110 mm when at rest. For example, in some embodiments the stent can have a relaxed diameter of 55 mm when the length of the stent is also 100 mm. If the stent is stretched to 150 mm, the diameter of the stent will then be reduced to 30 mm. Accordingly, the disclosed stent can be used for the treatment of various aortas with different diameters. For example, Table 1 below shows the length-diameter ratios of the disclosed stents as they relate to the human aorta anatomy.

TABLE 1

Length-Diameter Ratios

| | | Approx. Unit Measurements | |
|---|---|---|---|
| Device | Location | Diameter (mm) | Length (mm) |
| Ascyrus, 40 mm | Rest (40 mm) | 40 | 90 |
| | Max (35 mm) | 35 | 140 |
| | | 30 | 160 |
| | | 25 | 170 |
| | | 20 | 180 |
| Ascyrus, 55 mm | Rest (55 mm) | 55 | 115 |
| | Old Max (50 mm) | 50 | 170 |
| | New Max (45 mm) | 45 | 190 |
| | | 40 | 205 |
| | | 35 | 220 |
| | Min (30 mm) | 30 | 235 |

Stent 10 can be manufactured using any of a wide variety of methods known and used in the art. For example, in some embodiments, the stent can be manufactured by shape setting and creating each individual spiral strand individually prior to superimposing multiple spiral strands to create the hollow stent structure over a cylindrical structure or mandrel. Alternatively, the disclosed stent can be constructed by shape setting and creating multiple superimposing spiral strands to create a hollow stent structure over a mandrel prior to removing the mandrel. Thus, the strands can be bent or formed into shape on a mandrel while assembled into the self-expanding stent, or the strands can be bent or formed into shape before being assembled into the stent.

In some embodiments, stent 10 can be uncovered as shown in FIG. 3. However, the presently disclosed subject matter also includes embodiments wherein stent 10 is at least partially covered on the inside and/or outside of the stent with graft material. Suitable graft materials can include (but are not limited to) extracellular matrix and/or polymeric materials (e.g., polytetrafluoroethylene (PTFE), polyethylene terephthalate (PET), expanded polytetrafluoroethylene (ePTFE), polycarbonate urethane, polyurethane, polypropylene, polyethylene, silicone, silicone elastomers, polyolefins, and combinations thereof). In some embodiments, the graft material attached to the uncovered stent can also be supported by separate individual meandering strands or wires such as z- or m-stents. However, any supporting stent configuration can support the graft material. Specific graft materials can be selected based on performance criteria specific to an individual subject, such as pore size, percent open space, permeability, wall thickness, tensile strength, and the like.

The shape of spiral strands 5 in concert allows for creation of a stent that retains its physical properties, including kink-resistance and radial resistive force. Advantageously, the disclosed stent is also able to change its shape, diameter, and length to accommodate the corresponding shape, diameter, and length of subject's diseased vessel. For example, the disclosed stent is configured to be able to change its length and/or diameter to adjust to the diameter of a hollow tube. In some embodiments, the disclosed stent is configured to exert a minimal resistive force of at least 1 newton (N) despite changing its length and/or diameter. The term "resistive force" as used herein refers to a force opposing motion of an object by the user (e.g., such as the walls of the aorta). In some embodiments the disclosed stent can be configured to exert a maximum outward chronic force of about 7N despite changing its length and/or diameter. The term "outward chronic force" as used herein refers to a force having a direction generally outward, away from the object generating the force at rest.

In some embodiments, the disclosed stent can be attached to the proximal or distal portions of stent-reinforced grafts. Thus, in some embodiments stent 45 can comprise a collar engaged with one end of the stent. FIG. 3 depicts collar 55 engaged with first end 60 of the stent. The collar is configured to selectively engage with a stent-reinforced graft or with the aorta for securing stent 45 within the aorta. Any of the wide variety of stent collars known or used in the art can be used. The collar can be secured in place using known methods, such as by stitching or through the use of mechanical elements. In some embodiments, the first and second ends of each strand is configured to include eyelet 41 for enabling the stent to hook into the collar.

Figure 4:
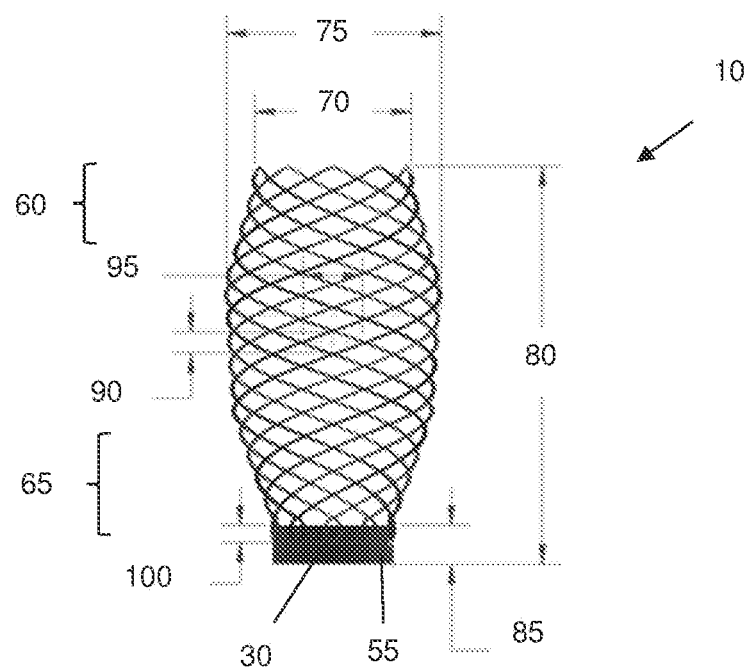
FIG. 4 is a perspective view of a tapered multi-spiral stent in accordance with some embodiments of the presently disclosed subject matter.

In some embodiments, multi-spiral stent 10 can comprise a tapering proximal, mid-, and/or distal sections to decrease the strain on the looping ends of the spiral strand during use under extreme conditions. Particularly, FIG. 4 illustrates one embodiment of stent 10 comprising tapered areas at first and second ends 60 and 65. Thus, as shown, the resting stent can have tapered diameter 70 at the first and/or second end of about 40 mm, and non-tapered diameter 75 of about 55 mm (e.g., at the middle portion of the stent). In some embodiments, the stent can have a resting length 80 of about 101 mm when attached to collar 55, and collar length 85 can be about 10 mm. Thus, the length of just the resting stent (with no attached collar) can be about 91 mm. In some embodiments, the disclosed stent can have longitudinal rise 90 between adjacent strands of about 5.4 mm. In some embodiments, the width between intersecting strands 95 can be about 15.4 mm. In some embodiments, the overlap length 100 between terminal bend 30 and collar 55 can be about 4.5 mm. However, it should be appreciated that the dimensions of stent 10 are not limited.

In some embodiments, the disclosed stent can be elongated to a length of at least about (or no more than about) 100% to 500% the resting (expanded) length (e.g., 100%, 125%, 150%, 175%, 200%, 225%, 250%, 275%, 300%, 325%, 350%, 375%, 400%, 425%, 450%, 475%, or 500%). The corresponding stent diameter can be correspondingly reduced by at least about 5-50% during expansion of the stent length (e.g., 5%, 10%, 15%, 20%, 25%, 30%, 35%, 40%, 45%, or 50%).

The presently disclosed stent can be used for endovascular aortic repair, including repair of aortic valve disease, aortic stenosis, ascending aortic aneurysms, aortic insufficiency, aortic regurgitation, ascending aneurysm, bicuspid valve disease, and/or aortic dissections. As set forth above, the disclosed stent advantageously can be altered in length and/or diameter to be sized for a wide variety of patient anatomies. To this end, the disclosed stent can be modified to accommodate standard, smaller-than-standard, and larger-than-standard sized aortas and other similar anatomical variations.

Figure 7A:
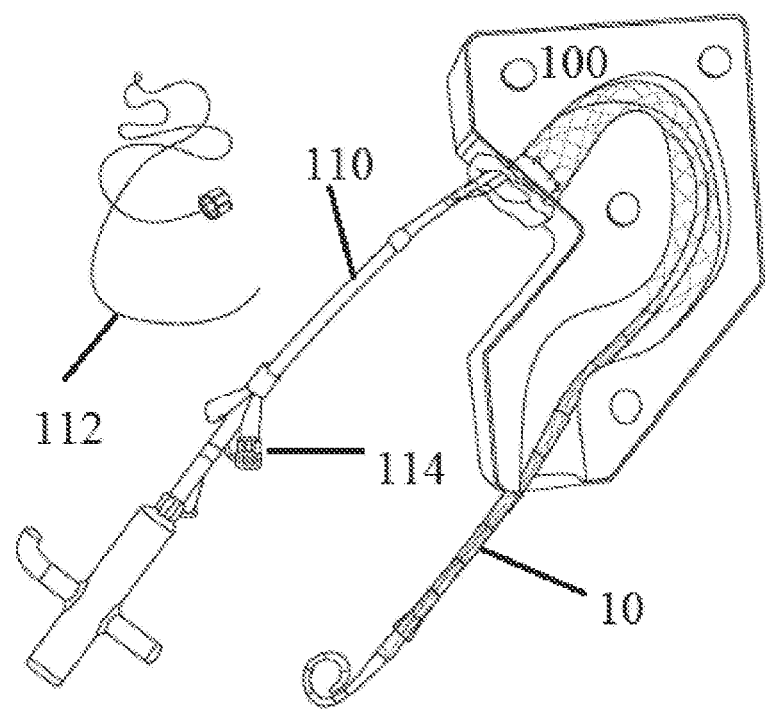
FIGS. 7a and 7b are perspective views of kits comprising a stent in accordance with some embodiments of the presently disclosed subject matter.
Figure 7B:
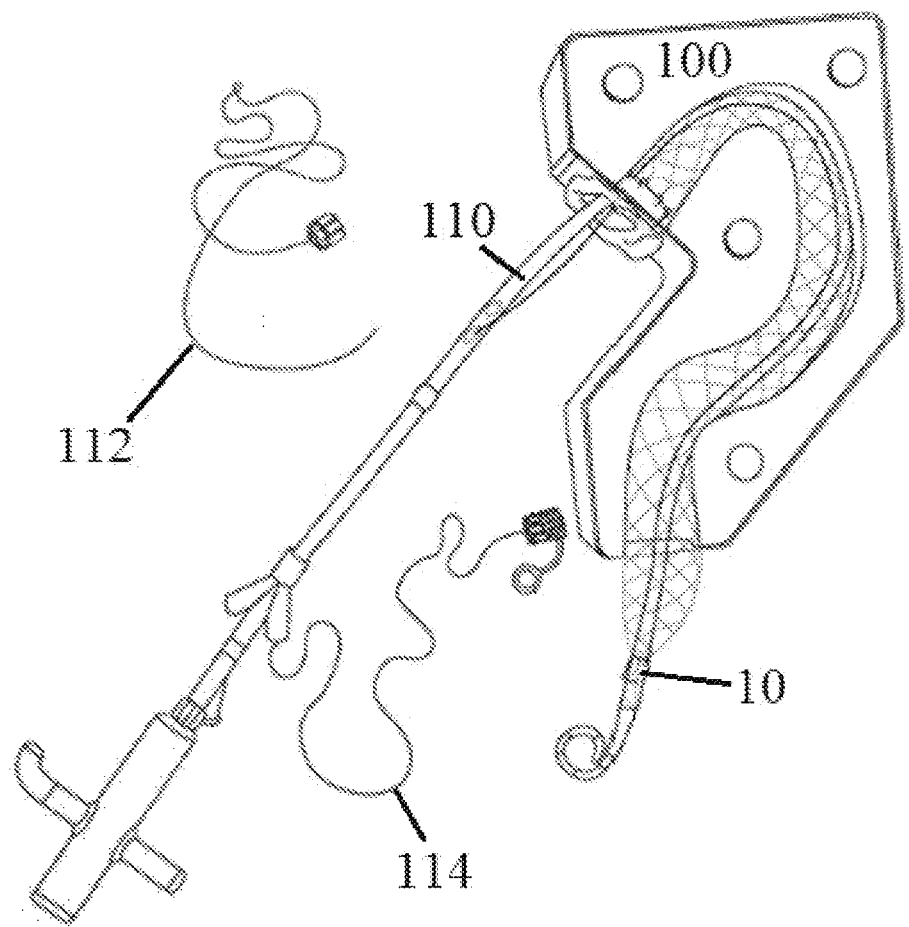

In some embodiments, stent 10 can be provided as part of a kit. Particularly, the kit can include the disclosed stent and a deployment device. A diameter of the stent device can be modified by translating of one end of the stent to thereby alter the length of the stent, resulting in modification of the stent diameter. This arrangement is represented well in FIGS. 7a and 7b.

Once stent device 10 and deployment device 110 have been inserted into the aorta (represented by mold 100 for illustration purposes), a first release wire 112 has been translated to expand a first segment of the stent device 10 and the deployment device 110 has been translated to fully deploy the first segment within the aorta, the second release wire 114 may be translated to begin expansion of the second segment of the stent device. Before fully translating the second release wire 114, the rod may again be translated to expand and position the stent device within the aorta by pulling or pushing on the stent device 10 once it has been anchored against the aorta. Other embodiments may show a single release wire or more release wires. The release wires are engaged with the stent 10 to keep the stent in a contracted state until deployment.

In other embodiments, the deployment apparatus can include a sheath (for housing the stent) and a guide rod passing through the center of the sheath for deploying the stent at an operational site. The sheath constrains the stent in a compressed state and the guide rod carries the stent device and is removable through the center of the stent when the stent is in an expanded state (e.g., upon removal of the sheath).

The disclosed stent offers several advantages over conventional z-shaped or braided stents. Particularly, the disclosed stent has the ability to easily change length and diameter and retain its original physical properties. Further, because the stent is able to accommodate changing diameters, far fewer sizes are needed to treat different vascular size ranges. In contrast, conventional stents typically require a large array of stents with predetermined diameters and lengths. In addition, by controlling the expansion of the stent by the operator, the different portions of the stent can be controlled and expanded to varying degrees to fit the stent to the patient's particular anatomy.

It should be appreciated that the presently disclosed subject matter has broad applications. The foregoing embodiments were chosen and described to illustrate principles of the methods and apparatuses as well as some practical applications. The preceding description enables others skilled in the art to utilize methods and apparatuses in various embodiments and with various modifications as are suited to the particular use contemplated. In accordance with the provisions of the patent statutes, the principles and modes of operation of this disclosure have been explained and illustrated in exemplary embodiments.

EXAMPLES

The following Examples have been included to provide guidance to one of ordinary skill in the art for practicing representative embodiments of the presently disclosed subject matter. In light of the present disclosure and the general level of skill in the art, those of skill can appreciate that the following Examples are intended to be exemplary only and that numerous changes, modifications, and alterations can be employed without departing from the scope of the presently disclosed subject matter.

Example 1

Construction of a Multi-Spiral, Self-Expanding Stent

A stent was constructed from 5 stainless steel strands by helically winding each strand longitudinal axis using a mandrel. The individual spiral strands were then superimposed multiple over a mandrel to create a hollow stent structure.

Example 2

After-Procedure Deployment of a Multi-Spiral, Self-Expanding Stent

Figure 5:
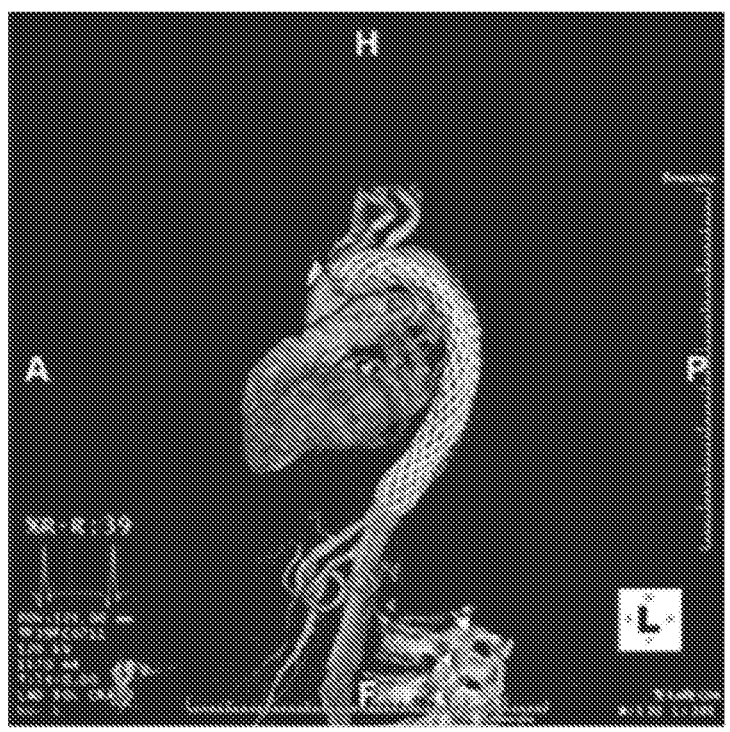
FIG. 5 is a CT scan of a 55 mm multi-spiral stent accommodating itself into an aorta measuring 45 mm proximally and 33 mm distally.

The stent of Example 1 was deployed in a patient. The after-procedure deployment is shown in the CT scan of FIG. 5. As shown, the stent accommodates itself into an aorta measuring 45 mm proximally and 33 mm distally.

Example 3

Before and After Images

Figure 6A:
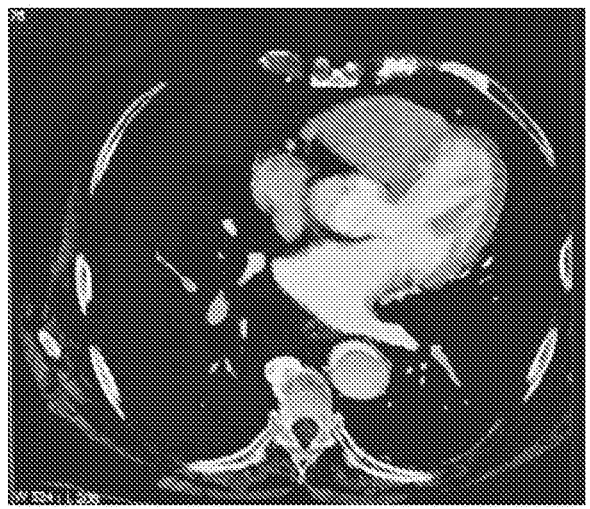
FIG. 6a is a CT scan of a dissected aorta with a slit-like narrowing of the true lumen and delamination of the aortic wall.
Figure 6B:
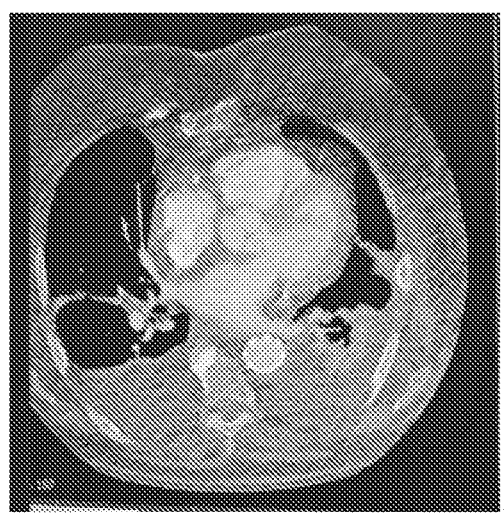

A patient with an aortic dissection was selected, as shown in FIG. 6a. Specifically, as shown in the CT scan of FIG. 6a, an aortic dissection is visible as the brighter contrast portion of the aorta. The stent of Example 1 was implanted in the patient. FIG. 6b illustrates the patient 4 days after the surgery. As shown in the CT scan, the brighter contrast portion represents the implanted stent device. Importantly, the diameter of the aorta has decreased by about a centimeter in the procedure, representing a significant improvement in overall aorta health.

Example 4

Crush Resistance Testing

A stent was constructed in accordance with Example 1, and assessed to determine resistance to compression. 10 units each of stents with diameters of 40-30 mm, 55 mm, and 55-40 mm were compressed with a flat plate to 50% of the free state diameter and released followed by diameter measurement to assess the ability of the stent to meet stent diameter post-crush. The results are shown in Table 2, below.

TABLE 2

Stent Crush Resistance Testing

| | Recovered Outside Diameter Stent | | | | | |
|---|---|---|---|---|---|---|
| | 40 mm 35-48 mm | 30 mm 25-38 mm | 55 mm 47-65 mm | 55 mm 47-65 mm | 55 mm 47-65 mm | 40 mm 35-48 mm |
| 1 | 38.94 | 26.36 | 57.36 | 52.56 | 57.20 | 38.03 |
| 2 | 39.36 | 27.78 | 57.68 | 53.08 | 57.23 | 38.93 |
| 3 | 37.68 | 26.94 | 57.51 | 52.95 | 57.64 | 40.09 |
| 4 | 38.67 | 28.27 | 57.35 | 53.53 | 57.54 | 39.78 |
| 5 | 38.92 | 27.89 | 57.49 | 52.94 | 57.14 | 39.21 |
| 6 | 39.99 | 28.73 | 57.97 | 52.53 | 57.26 | 39.42 |
| 7 | 37.44 | 26.73 | 57.31 | 52.78 | 57.79 | 38.14 |
| 8 | 38.45 | 28.95 | 57.49 | 53.89 | 57.13 | 39.06 |
| 9 | 39.20 | 28.23 | 57.83 | 52.84 | 57.42 | 38.02 |
| 10 | 39.15 | 27.66 | 58.25 | 52.83 | 56.80 | 38.87 |
| Mean | 38.78 | 27.75 | 57.62 | 52.99 | 57.32 | 38.96 |
| Std Dev | 0.766 | 0.854 | 0.307 | 0.422 | 0.288 | 0.720 |
| 95/90 Min | 36.60 | 25.33 | 56.90 | 52.00 | 56.64 | 37.26 |
| 95/90 Max | 40.96 | 30.18 | 58.35 | 53.99 | 57.99 | 40.65 |

Conclusion

As shown in Table 2, the stents demonstrated an ability to recover to an acceptable level after crush resistance, indicating that the compression resistance of the implant is sufficient for the intended use with 95% confidence and 90% reliability.

Example 5

Chronic Outward and Radial Resistive Force Testing 10 units of 40-30 mm diameter stents and 10 units of 50-40 mm diameter stents constructed in accordance with Example 1 were obtained and used to assess the chronic outward force acting on the artery to maintain dissection tacking and radial resistive force to resist collapse. Each test stent was radially reduced from free-state to 10% below minimum treatment diameter, then released to free state. The radial resistive force and chronic outward force were measured at the minimum and maximum treatment diameter. The acceptance criteria was radial resistance force at the smallest treatment diameter greater than or equal to a control device (a Medtronic Valiant Thoracic Stent), and the chronic outward force at the smallest treatment diameter less than or equal to 5 Newtons (N), based on arterial strength estimated at 10 N.

TABLE 3

Stent Crush Resistance Testing

| | Min Radial Resistive Force (N) | | | Max Outward Chronic Force (N) | |
|---|---|---|---|---|---|
| Size | Control | 40-30 mm | 55-40 mm | 40-30 mm | 55-40 mm |
| Spec | | ≥0.642 N | | ≤5 N | |
| 1 | 0.976 | 2.377 | 1.916 | 0.343 | 0.728 |
| 2 | 0.976 | 2.505 | 2.458 | 0.238 | 0.798 |
| 3 | 0.814 | 2.606 | 1.986 | 0.329 | 0.587 |
| 4 | — | 2.476 | 2.410 | 0.664 | 0.690 |
| 5 | — | 2.619 | 2.445 | 0.686 | 0.773 |
| 6 | — | 2.633 | 2.261 | 0.291 | 0.746 |
| 7 | — | 2.517 | 2.094 | 0.058 | 0.715 |
| 8 | — | 3.001 | 2.470 | 0.506 | 0.620 |

TABLE 3-continued

Stent Crush Resistance Testing

| | Min Radial Resistive Force (N) | | | Max Outward Chronic Force (N) | |
|---|---|---|---|---|---|
| Size | Control | 40-30 mm | 55-40 mm | 40-30 mm | 55-40 mm |
| 9 | — | 2.402 | 2.561 | 0.416 | 0.713 |
| 10 | — | 2.315 | 2.396 | 0.422 | 0.651 |
| Mean | 0.922 | 2.545 | 2.300 | 0.395 | 0.702 |
| Std Dev | 0.093 | 0.193 | 0.225 | 0.191 | 0.067 |
| Mean-3*SD | 0.642 | — | — | — | — |
| 95/90 Min | — | 2.092 | 2.300 | — | — |
| 95/90 Max | — | — | — | 0.844 | 0.859 |

Conclusion

As shown in Table 3, the stents demonstrated equal to higher radial resistive force and equal to lower outward chronic force than the acceptance criteria and are considered sufficient for the intended use with 95% confidence and 90% reliability.

Example 6

Stent Kink Resistance Testing

Test stents constructed in accordance with Example 1 were obtained. 10 units each of stents with diameters of 40 mm and 55 mm were used. 5 units each of stents with diameters of 40-30 mm and 55-40 mm were used. Each test article had a proximal end of stent bend of about 1 inch radius. The stents were evaluated for retained stent lumen while in the radius. Lumen maintained at greater than 50% of the free state diameter with 95% confidence and 90% reliability were considered an accepted stent. The results of the testing are shown below in Table 4.

TABLE 4

Stent Kink Resistance Results

| | Retained lumen | | | |
|---|---|---|---|---|
| Size | 40 mm | 55 mm | 40-30 mm | 55-40 mm |
| Spec. (mm) | ≥20 | ≥27.5 | ≥20 | ≥27.5 |
| 1 | Pass | Pass | Pass | Pass |
| 2 | Pass | Pass | Pass | Pass |
| 3 | Pass | Pass | Pass | Pass |
| 4 | Pass | Pass | Pass | Pass |
| 5 | Pass | Pass | Pass | Pass |
| 6 | Pass | Pass | — | — |
| 7 | Pass | Pass | — | — |
| 8 | Pass | Pass | — | — |
| 9 | Pass | Pass | — | — |
| 10 | Pass | Pass | — | — |

Conclusion

As shown in Table 4, the stents demonstrated the ability to withstand kinking with 95% confidence and 90% reliability.

Example 7

Durability Assessment by Finite Element Analysis

Computational analysis was used to predict fatigue life. Analysis included primary cyclic motion of the aortic arch and descending aorta include pulsation of both the arch and descending aorta, as well as cyclic bending of the arch region. Results from the analysis included the peak strain during crimp, as well as the mean and alternating strains during cyclic loading. The strains were used to assess the potential for device fracture by comparing to the appropriate material strength properties. Acceptance criteria was determined as peak strain during crimping of <10%, cyclic loading mean strain<7% and strain amplitude<0.4%. The results are given below in Tables 5 and 6.

TABLE 5

Peak Max Principal Crimp Strain

|  | Peak Max Principal Crimp Strain | Overload Factor of Safety |
|---|---|---|
| Spec. | <10% | N/A |
| 40 mm Straight | 9.10% | 4.4 |
| 40 mm Tapered | 9.30% | 4.3 |
| 55 mm Straight | 9.56% | 4.2 |
| 55 mm Tapered | 9.74% | 4.1 |

TABLE 6

Corresponding Mean and Corresponding Amp

| Treatment Vessel |  | Peak Max Principal Strain Amplitude (Corresponding Mean) | Peak Max Principal Mean Strain (Corresponding Amp.) | Fatigue Safety Factor (FSF) |
|---|---|---|---|---|
| Spec. |  | <0.4% | <7% |  |
| 40 mm Straight | Min | 0.239% (6.67%) | 6.73% (0.230%) | 1.63 |
| 40 mm Straight | Max | 0.143% (0.675%) | 0.80% (0.134%) | 2.73 |
| 40 mm Tapered | Min | 0.169% (5.766%) | 5.77% (0.169%) | 2.31 |
| 40 mm Tapered | Max | 0.118% (0.709%) | 0.91% (0.094%) | 3.31 |
| 55 mm Straight | Min | 0.221% (1.889%) | 6.87% (0.181%) | 1.76 |
| 55 mm Straight | Max | 0.168% (3.73%) | 3.73% (0.168%) | 2.32 |
| 55 mm Tapered | Min | 0.203% (6.53%) | 6.53% (0.203%) | 1.92 |
| 55 mm Tapered | Max | 0.159% (1.04%) | 1.70% (0.139%) | 2.45 |

Conclusion

The analysis results indicated peak crimp strains in the four devices ranging between 9.1% and 9.74%. Compared to an ultimate strain of 40%, the crimp strains correspond to overload safety factors ranging between 4.1 and 4.4. Under combined cyclic pulsation and bending, the peak strain amplitudes for the four devices ranged 0.118% (40 mm tapered, max vessel) to 0.239% (40 mm straight, minimum vessel). Fatigue safety factors for each configuration analyzed were determined by comparing the experimental determined fatigue strength of 0.39% to the peak strain amplitude. The minimum safety factor (for the 40 mm straight device in its minimum vessel) was 1.63. Based on this comprehensive analysis, the stent met all acceptance criteria and was considered safe for intended use.

What is claimed is:

1. A multi-spiral self-expanding stent comprising:
a plurality of strands, each strand including a first strand portion extending from a first strand end to a terminal bend, a second strand portion extending from the terminal bend to a second strand end, the first strand end and second strand end concluding in a plane at a first end of the self-expanding stent, and a first open eyelet disposed at the first strand end and a second open eyelet disposed at the second strand end,
wherein the first and second strand portions are woven together to form the self-expanding stent,
wherein the first and second strand portions forming each of the strands are formed of a continuous material, and
wherein the first strand portion of each strand bends in one spiral direction to the terminal bend, and the second strand portion bends in an opposite spiral direction after the terminal bend; and
a graft collar secured to the first open eyelet and second open eyelet of each of the plurality of strands,
wherein the first open eyelet and the second open eyelet are hooked through the graft collar.

2. The multi-spiral self-expanding stent of claim 1, wherein the graft collar extends beyond the plane at the first end of the self-expanding stent in a direction opposite the terminal bends of each of the plurality of strands.

3. The multi-spiral self-expanding stent of claim 1, wherein the graft collar is configured to be secured in a body lumen of a patient.

4. The multi-spiral self-expanding stent of claim 1, wherein the graft collar is configured to be secured in an aorta of a patient.

5. The multi-spiral self-expanding stent of claim 1, wherein the self-expanding stent is covering-free between the graft collar a second end of the self-expanding stent.

6. The multi-spiral self-expanding stent of claim 1, wherein the strands are formed of one or more metals.

7. The multi-spiral self-expanding stent of claim 6, wherein the one or more metals comprise stainless steel, gold, cobalt, chromium, molybdenum, nickel, titanium, nitinol, or alloys thereof.

8. The multi-spiral self-expanding stent of claim 1, wherein the strands are formed of one or more polymeric materials.

9. The multi-spiral self-expanding stent of claim 8, wherein the one or more polymeric materials comprise polypropylene, polycarbonate, nylon, high density polyethylene, or combinations thereof.

10. The multi-spiral self-expanding stent of claim 1, wherein the strands are bent or formed into shape on a mandrel while assembled into the self-expanding stent.

11. The multi-spiral self-expanding stent of claim 1, wherein the strands are bent or formed into shape before being assembled into the self-expanding stent.

12. The multi-spiral self-expanding stent of claim 1, wherein the self-expanding stent is configured to:
a) change its length and diameter to adjust itself to the diameter of a hollow tube;
b) exert a minimal radial resistive force of at least 1N despite changing its length and diameter; and
c) exert a maximum outward chronic force of 7N despite changing its length and diameter.

13. The multi-spiral self-expanding stent of claim 1, further comprising a tapered section.

14. The multi-spiral self-expanding stent of claim 13, wherein the tapered section is positioned at the first end of the self-expanding stent.

15. The multi-spiral self-expanding stent of claim 13, wherein the tapered section is positioned at a second end-of the self-expanding stent.

16. The multi-spiral self-expanding stent of claim 13, wherein the tapered section is positioned along a middle of the self-expanding stent between the first end and a second-end of the self-expanding stent.

17. The multi-spiral self-expanding stent of claim 1, further comprising:

a first tapered section positioned at the first end of the self-expanding stent;

a second tapered section positioned at a second end of the self-expanding stent; and a non-tapered section positioned between the first tapered section and the second tapered section.

18. The multi-spiral self-expanding stent of claim 1, wherein the graft collar comprises a flange extending radially outward relative to a longitudinal axis of the self-expanding stent.

19. The multi-spiral self-expanding stent of claim 1, wherein the plurality of strands comprises at least four strands.

20. The multi-spiral self-expanding stent of claim 1, wherein the plurality of strands comprises five stainless steel strands.

* * * * *